(12) United States Patent
Niemiec et al.

(10) Patent No.: US 8,545,566 B2
(45) Date of Patent: Oct. 1, 2013

(54) ARTICULATING SPACER

(75) Inventors: Marcin Niemiec, Bridgeport, PA (US); Mark Adams, Downingtown, PA (US); Andrew Iott, Villanova, PA (US)

(73) Assignee: Globus Medical, Inc., Audubon, PA (US)

( * ) Notice: Subject to any disclaimer, the term of this patent is extended or adjusted under 35 U.S.C. 154(b) by 133 days.

(21) Appl. No.: 13/109,754

(22) Filed: May 17, 2011

(65) Prior Publication Data

US 2011/0276142 A1 Nov. 10, 2011

Related U.S. Application Data

(63) Continuation-in-part of application No. 12/250,168, filed on Oct. 13, 2008, now Pat. No. 8,147,554.

(51) Int. Cl.
*A61F 2/44* (2006.01)

(52) U.S. Cl.
USPC .................................................. 623/17.16

(58) Field of Classification Search
USPC ............... 623/17.11–17.16, 18.11; 606/60, 606/246–249, 276–279, 62, 99
See application file for complete search history.

(56) References Cited

U.S. PATENT DOCUMENTS

| | | | |
|---|---|---|---|
| 5,401,269 A * | 3/1995 | Buttner-Janz et al. | 623/17.15 |
| 5,800,550 A * | 9/1998 | Sertich | 623/17.16 |
| 6,176,882 B1 * | 1/2001 | Biedermann et al. | 623/17.15 |
| 6,179,874 B1 * | 1/2001 | Cauthen | 623/17.14 |
| 6,193,756 B1 * | 2/2001 | Studer et al. | 623/17.15 |
| 6,375,682 B1 * | 4/2002 | Fleischmann et al. | 623/17.12 |
| 6,520,991 B2 * | 2/2003 | Huene | 623/17.11 |
| 6,527,803 B1 * | 3/2003 | Crozet et al. | 623/17.11 |
| 6,752,832 B2 * | 6/2004 | Neumann | 623/17.15 |
| 6,793,678 B2 * | 9/2004 | Hawkins | 623/17.15 |
| 7,018,415 B1 * | 3/2006 | McKay | 623/17.15 |
| 7,044,970 B2 * | 5/2006 | Errico et al. | 623/17.14 |
| 7,060,073 B2 * | 6/2006 | Frey et al. | 606/85 |
| 7,118,599 B2 | 10/2006 | Errico | |
| 7,128,760 B2 * | 10/2006 | Michelson | 623/17.15 |
| 7,223,292 B2 * | 5/2007 | Messerli et al. | 623/17.16 |
| 7,407,513 B2 * | 8/2008 | Alleyne et al. | 623/17.16 |
| 7,410,501 B2 * | 8/2008 | Michelson | 623/17.15 |
| 7,470,273 B2 * | 12/2008 | Dougherty-Shah | 606/86 A |
| 7,566,346 B2 * | 7/2009 | Kirschman | 623/17.14 |
| 7,621,956 B2 * | 11/2009 | Paul et al. | 623/17.15 |
| 7,637,956 B2 * | 12/2009 | Lechmann et al. | 623/17.15 |
| 7,655,046 B2 * | 2/2010 | Dryer et al. | 623/17.15 |
| 7,708,778 B2 * | 5/2010 | Gordon et al. | 623/17.15 |
| 7,708,779 B2 * | 5/2010 | Edie et al. | 623/17.15 |
| 7,717,960 B2 * | 5/2010 | Schneier | 623/17.15 |
| 7,753,958 B2 * | 7/2010 | Gordon et al. | 623/17.15 |
| 7,776,091 B2 * | 8/2010 | Mastrorio et al. | 623/17.15 |
| 7,794,501 B2 * | 9/2010 | Edie et al. | 623/17.12 |
| 7,828,849 B2 * | 11/2010 | Lim | 623/17.16 |

(Continued)

*Primary Examiner* — Alvin J. Stewart (57) ABSTRACT

Spinal implants are disclosed. One spinal implant includes a support body, an articulating element, a blocking member and a motion limiting member. The support body includes a superior end surface and a lower end surface having teeth. In between the superior end surface and the lower end surface is a recess formed in a sidewall of the support body for receiving the articulating element. The blocking member can be received in the recess to prevent inadvertent back-out of the articulating element from within the recess. The articulating element can articulate in one or more directions, thereby allowing articulation of the spinal implant into a desired position within a disc space.

18 Claims, 9 Drawing Sheets

(56) References Cited

U.S. PATENT DOCUMENTS

| | | | |
|---|---|---|---|
| 7,901,458 B2* | 3/2011 | DeRidder et al. | 623/17.11 |
| 7,959,675 B2* | 6/2011 | Gately | 623/17.11 |
| 7,998,212 B2* | 8/2011 | Schwab et al. | 623/17.16 |
| 8,002,837 B2* | 8/2011 | Stream et al. | 623/17.16 |
| 8,012,156 B2* | 9/2011 | Marquez Alvarez | 606/99 |
| 8,052,754 B2* | 11/2011 | Froehlich | 623/17.16 |
| 8,062,375 B2* | 11/2011 | Glerum et al. | 623/17.16 |
| 8,070,813 B2* | 12/2011 | Grotz et al. | 623/17.11 |
| 8,075,593 B2* | 12/2011 | Hess | 606/248 |
| 8,118,871 B2* | 2/2012 | Gordon et al. | 623/17.16 |
| 8,128,700 B2* | 3/2012 | Delurio et al. | 623/17.15 |
| 8,133,232 B2* | 3/2012 | Levy et al. | 606/90 |
| 8,147,550 B2* | 4/2012 | Gordon et al. | 623/17.15 |
| 8,147,554 B2* | 4/2012 | Hansell et al. | 623/17.16 |
| 8,157,864 B2* | 4/2012 | Rogeau et al. | 623/17.16 |
| 8,187,332 B2* | 5/2012 | McLuen | 623/17.16 |
| 8,192,496 B2* | 6/2012 | Peukert et al. | 623/17.15 |
| 8,211,175 B2* | 7/2012 | Eisermann et al. | 623/17.14 |
| 8,216,317 B2* | 7/2012 | Thibodeau | 623/17.16 |
| 8,231,680 B2* | 7/2012 | Bullard | 623/17.16 |
| 8,241,364 B2* | 8/2012 | Hansell et al. | 623/17.16 |
| 8,252,060 B2* | 8/2012 | Hansell et al. | 623/17.16 |
| 8,257,440 B2* | 9/2012 | Gordon et al. | 623/17.15 |
| 8,257,442 B2* | 9/2012 | Edie et al. | 623/17.15 |
| 8,262,736 B2* | 9/2012 | Michelson | 623/17.16 |
| 8,273,126 B2* | 9/2012 | Lindner | 623/17.15 |
| 8,273,129 B2* | 9/2012 | Baynham et al. | 623/17.16 |
| 8,292,962 B2* | 10/2012 | Gornet et al. | 623/17.16 |
| 8,366,777 B2* | 2/2013 | Matthis et al. | 623/17.16 |
| 8,377,133 B2* | 2/2013 | Yuan et al. | 623/17.15 |
| 8,382,843 B2* | 2/2013 | Laurence et al. | 623/17.16 |
| 8,388,684 B2* | 3/2013 | Bao et al. | 623/17.14 |
| 2002/0138146 A1 | 9/2002 | Jackson | 623/17.15 |
| 2004/0153065 A1* | 8/2004 | Lim | 606/53 |
| 2004/0153156 A1* | 8/2004 | Cohen et al. | 623/17.13 |
| 2005/0085917 A1* | 4/2005 | Marnay et al. | 623/17.16 |
| 2005/0096745 A1* | 5/2005 | Andre et al. | 623/17.11 |
| 2008/0091211 A1* | 4/2008 | Gately | 606/99 |
| 2008/0133013 A1* | 6/2008 | Duggal et al. | 623/17.16 |
| 2008/0221693 A1* | 9/2008 | Brehm et al. | 623/17.16 |
| 2008/0221694 A1* | 9/2008 | Warnick et al. | 623/17.16 |
| 2008/0234686 A1* | 9/2008 | Beaurain et al. | 606/90 |
| 2009/0076607 A1* | 3/2009 | Aalsma et al. | 623/17.16 |
| 2009/0076608 A1* | 3/2009 | Gordon et al. | 623/17.16 |
| 2009/0088850 A1* | 4/2009 | Froehlich | 623/17.16 |
| 2009/0143859 A1* | 6/2009 | McClellan et al. | 623/17.16 |
| 2009/0216330 A1* | 8/2009 | Geisert et al. | 623/17.16 |
| 2009/0248092 A1* | 10/2009 | Bellas et al. | 606/86 A |
| 2009/0265008 A1* | 10/2009 | Thibodeau | 623/17.16 |
| 2009/0276049 A1* | 11/2009 | Weiland | 623/17.16 |
| 2009/0326656 A1* | 12/2009 | de Villiers et al. | 623/17.15 |
| 2010/0004746 A1* | 1/2010 | Arramon | 623/17.15 |
| 2010/0023128 A1* | 1/2010 | Malberg | 623/17.16 |
| 2010/0070036 A1* | 3/2010 | Implicito | 623/17.16 |
| 2010/0082110 A1* | 4/2010 | Belliard | 623/17.16 |
| 2010/0094422 A1* | 4/2010 | Hansell et al. | 623/17.16 |
| 2010/0145455 A1* | 6/2010 | Simpson et al. | 623/17.16 |
| 2010/0168862 A1* | 7/2010 | Edie et al. | 623/17.16 |
| 2010/0185286 A1* | 7/2010 | Allard et al. | 623/17.11 |
| 2010/0185287 A1* | 7/2010 | Allard et al. | 623/17.11 |
| 2010/0185288 A1* | 7/2010 | Carls et al. | 623/17.11 |
| 2010/0191337 A1* | 7/2010 | Zamani et al. | 623/17.16 |
| 2010/0256763 A1* | 10/2010 | Sournac et al. | 623/17.16 |
| 2010/0256764 A1* | 10/2010 | Tsuang et al. | 623/17.16 |
| 2010/0262245 A1* | 10/2010 | Alfaro et al. | 623/17.16 |
| 2010/0262246 A1* | 10/2010 | Attia | 623/17.16 |
| 2010/0298941 A1* | 11/2010 | Hes et al. | 623/17.16 |
| 2010/0305706 A1* | 12/2010 | Webb et al. | 623/17.16 |
| 2011/0009970 A1* | 1/2011 | Puno | 623/17.16 |
| 2011/0054621 A1* | 3/2011 | Lim | 623/17.16 |
| 2011/0112644 A1* | 5/2011 | Zilberstein et al. | 623/17.15 |
| 2011/0144754 A1* | 6/2011 | Chee et al. | 623/17.16 |
| 2011/0172716 A1* | 7/2011 | Glerum | 606/279 |
| 2011/0172776 A1* | 7/2011 | Warnick et al. | 623/17.16 |
| 2011/0238185 A1* | 9/2011 | Filippi et al. | 623/17.16 |
| 2011/0270398 A1* | 11/2011 | Grotz et al. | 623/17.12 |
| 2011/0270402 A1* | 11/2011 | Frey et al. | 623/17.16 |
| 2011/0276142 A1* | 11/2011 | Niemiec et al. | 623/17.16 |
| 2011/0282457 A1* | 11/2011 | Daniele et al. | 623/17.16 |
| 2011/0301711 A1* | 12/2011 | Palmatier et al. | 623/17.16 |
| 2011/0319998 A1* | 12/2011 | O'Neil et al. | 623/17.16 |
| 2012/0010715 A1* | 1/2012 | Spann | 623/17.16 |
| 2012/0010716 A1* | 1/2012 | Spann | 623/17.16 |
| 2012/0010717 A1* | 1/2012 | Spann | 623/17.16 |
| 2012/0116512 A1* | 5/2012 | Sournac et al. | 623/17.16 |
| 2012/0165943 A1* | 6/2012 | Mangione et al. | 623/17.16 |
| 2012/0165945 A1* | 6/2012 | Hansell et al. | 623/17.16 |
| 2012/0191194 A1* | 7/2012 | Olmos et al. | 623/17.16 |
| 2012/0209386 A1* | 8/2012 | Triplett et al. | 623/17.16 |
| 2012/0226357 A1* | 9/2012 | Varela | 623/17.16 |
| 2012/0232659 A1* | 9/2012 | Himmelberger et al. | 623/17.16 |
| 2012/0232663 A1* | 9/2012 | Zipnick | 623/17.16 |
| 2012/0245695 A1* | 9/2012 | Simpson et al. | 623/17.16 |
| 2012/0277866 A1* | 11/2012 | Kalluri et al. | 623/17.16 |
| 2012/0277869 A1* | 11/2012 | Siccardi et al. | 623/17.16 |
| 2012/0316652 A1* | 12/2012 | Renganath et al. | 623/17.16 |
| 2013/0013069 A1* | 1/2013 | de Villiers et al. | 623/17.15 |
| 2013/0085573 A1* | 4/2013 | Lemoine et al. | 623/17.16 |
| 2013/0096685 A1* | 4/2013 | Ciupik et al. | 623/17.16 |

* cited by examiner

ARTICULATING SPACER

CROSS REFERENCE TO RELATED APPLICATIONS

This patent application is a continuation-in-part application claiming priority to U.S. patent application Ser. No. 12/250,168 filed on Oct. 13, 2008 now U.S. Pat. No. 8,147,554, the entire contents of which are incorporated by reference.

FIELD OF THE INVENTION

The present application generally relates to intervertebral spacers, and in particular, to articulating intervertebral spacers.

BACKGROUND OF THE INVENTION

The vertebrate spine is the axis of the skeleton providing structural support for the other parts of the body. Adjacent vertebrae of the spine are supported by an intervertebral disc, which serves as a mechanical cushion permitting controlled motion between vertebral segments of the axial skeleton. The intervertebral disc is a unique structure comprised of three components: the nucleus pulposus ("nucleus"), the annulus fibrosus ("annulus") and two vertebral end plates.

The spinal disc can be displaced or damaged due to trauma, disease, degenerative defects or wear over an extended period of time. For example, disc herniation occurs when annulus fibers are weakened or torn and the inner tissue of the nucleus becomes permanently bulged. The mass of a herniated or "slipped" nucleus tissue can compress a spinal nerve, resulting in leg pain, loss of muscle control, or even paralysis. In addition, in some cases, a degenerated nucleus can lose its water binding ability and deflate, thereby reducing the height of the nucleus and causing the annulus to buckle in certain areas.

To alleviate back pain caused by disc herniation or degeneration, the disc can be removed and replaced by an implant that promotes fusion of the remaining bone anatomy. The implant, such as a spacer or cage body, should be sufficiently strong to support the spine under a wide range of loading conditions. The implant should also be configured so that it is likely to remain in place once it has been positioned in the spine by the surgeon. In addition, the implant should be capable of being delivered minimally invasively or at least through a relatively small incision into a desired position.

Thus, there remains a need for an improved implant that addresses these difficulties.

SUMMARY OF THE INVENTION

Various embodiments of spinal implants are provided. In one embodiment, a spinal implant comprises a support body having a superior end surface and an inferior end surface, wherein each of the superior end surface and the inferior end surface include one or more teeth. The spinal implant includes a side recess formed in the support body in between the superior end surface and the inferior end surface for receiving an articulating element therethrough. In addition, the spinal implant includes an articulating element positioned in the recess, wherein the articulating element is configured to rotate along one or more axes.

In another embodiment, a spinal implant comprises a support body having a superior end surface and an inferior end surface. The spinal implant includes a side recess formed in the support body in between the superior end surface and the inferior end surface for receiving an articulating element therethrough. The spinal implant further includes an articulating element sized for insertion through the recess and configured to rotate along one or more axes, as well as a blocking member configured to be positioned within the recess for preventing back-out of the articulating element from within the recess.

In another embodiment, a spinal implant comprises a support body having a superior end surface and an inferior end surface, wherein each of the superior end surface and the inferior end surface includes one or more teeth, and wherein the support body includes a proximal end portion and a distal end portion having a tapered surface. A longitudinal opening can be formed through the support body, wherein the longitudinal opening is configured to receive a bone graft material. A side recess is formed in the support body between the superior end surface and the inferior end surface. The implant further comprises an articulating element sized and shaped to be received in the recess, the articulating element including an aperture with threads for receiving a portion of an insertion tool and a groove on a top portion thereof. A blocking member can be insertable through an aperture in the support body. The blocking member can be configured to prevent unintentional back-out of the articulating element from within the recess of the support body. In addition, a motion limiting member can be insertable through an aperture in the support body. The motion limiting member can be configured to contact the groove of the articulating element and to prevent over-articulation of the articulating element within the recess of the support body.

DETAILED DESCRIPTION OF THE ILLUSTRATED EMBODIMENTS

Detailed embodiments of the invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present application generally relates to implants such as intervertebral spacers, and in particular, to articulating intervertebral spacers. The implants can be used to fuse together a treated area of the spine while restoring or maintaining the proper spacing and natural curvature of the spine. The treated area can include regions between adjacent vertebral bodies so that the height of the implant corresponds approximately to the height of the disc. Advantageously, the improved implants described herein are configured to articulate with ease into a desired position in between two vertebrae. In some embodiments, the improved implants can articulate along multiple axes, thereby providing greater flexibility when positioning the spacer is a desired location. Novel features of the implants allow for more efficient insertion or placement of the implants into a desired position in between vertebrae.

Figure 1:
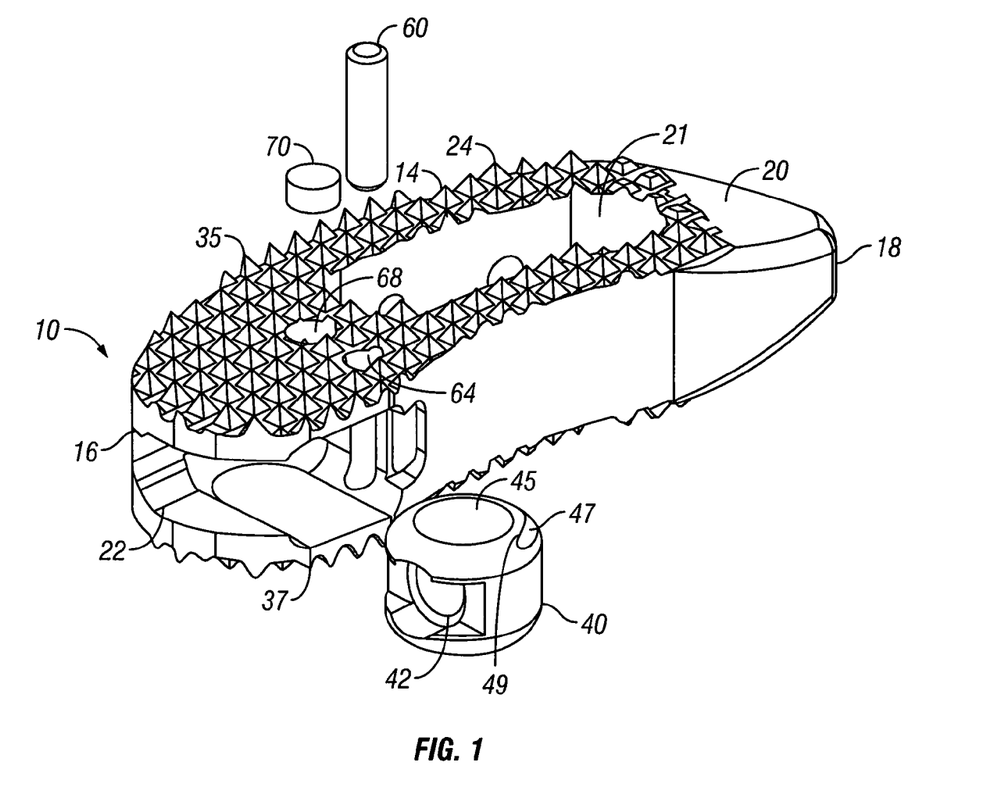
FIG. 1 is a perspective exploded view of an implant according to some embodiments.

FIG. 1 is a perspective exploded view of a spacer implant according to some embodiments. The implant 10, which is configured to fit into a disc space in between two vertebrae, comprises a support body 14, an articulating element 40, a blocking member 60, and a motion limiting member 70.

The support body 14 of the implant 10 includes a superior end surface 35 for contacting a superior vertebra and an inferior end surface 37 for contacting an inferior vertebra. On the superior and/or inferior end surfaces are one or more teeth 24 designed to contact the adjacent vertebrae and keep the support body 14 in a desired position. Also formed within the superior and/or inferior end surfaces are one or more longitudinal openings 21. The one or more longitudinal openings 21 can be formed through partly or completely through the implant 10, and are configured to receive bone graft or other natural and/or synthetic material to facilitate bone growth when implanted. In addition, on the superior and/or inferior end surfaces are one or more apertures—aperture 64 for receiving a blocking member 60 and aperture 68 for receiving a motion limiting member 70, which are discussed in more detail below.

In addition, the support body 14 includes a proximal end portion 16 and a distal end portion 18. As shown in FIG. 1, the distal end portion 18 can have a tapered surface 20. In alternative embodiments, the proximal end portion 16 can have a tapered surface instead of or in addition to the distal end portion. In some embodiments, when placing a support body 14 in between vertebrae, the distal end portion 18 with the tapered surface 20 can serve as the leading portion that is positioned in a disc space. Advantageously, the tapered surface 20 assists in self-distraction of vertebral bodies when the support body 14 is inserted in between vertebrae.

As shown in FIG. 1, the support body 14 also includes a side cut-out section or recess 22 formed on a curved sidewall of the support body 14. The recess 22 defines a space that is configured to receive an articulating element 40 therein. Compared to other spacer implants, in which articulating elements may be implanted through a portion of the superior end surface 35 and/or inferior end surface 37, the support body 14 of the present application advantageously provides a side entrance for the articulating element 40, thereby reducing the need to machine an aperture through the teeth 24. This advantageously preserves the number of teeth and/or surface area covered by teeth and increases the ability of the spacer to remain secure within a disc space.

During use, the articulating element 40 of the implant 10 can remain in the recess 22 of the implant 10. The articulating element 40 advantageously allows the support body 14 to be rotated in one or more axes (as shown in FIGS. 8A-8D), thereby allowing the support body 14 to be in a proper orientation and location within a disc space. To prevent the articulating element 40 from falling out of the implant 10, a blocking member 60 can be provided, as discussed further below.

The articulating element 40 comprises an aperture 42, a pair of substantially flat surfaces 45 and a groove 47 that extends along an upper portion of the articulating element 40. When the articulating element 40 is positioned within the recess 22 of the support body 14, the substantially flat surfaces 45 face inner walls of the support body 14. In between the substantially flat surfaces 45 of the articulating element 40 is an aperture 42 for receiving a mateable portion of a delivery instrument 100 (as shown in FIGS. 8A-8D). In some embodiments, when the mateable portion of the delivery instrument 100 is attached to the articulating element 40, the articulating element 40 allows the support body 14 to articulate or rotate relative to an axis of the delivery instrument, thereby allowing the support body 14 to be placed in a desired position in a disc space, as shown in FIGS. 8A-8D. In some embodiments, the aperture 42 of the articulating element 40 includes a plurality of internal threads (not shown) that mate with external threads of a portion of a delivery instrument. Advantageously, the articulating element 40 can articulate along one or more axes that extend across the aperture 42 when the articulating element 40 is positioned within the support body 14.

In some embodiments, the aperture 42 extends completely through a diameter of articulating element 40. In other embodiments, the aperture 42 extends through only a portion of a diameter of the articulating element 40. In some embodiments, the articulating element 40 comprises two separate apertures 42 that are formed on opposite sides of the articulating element 40.

A recess or groove 47 is formed along a portion of a top surface of the articulating element 47. The groove 47 is configured to contact a motion limiting member 70 that is received through the aperture 68. With the motion limiting member 70 in the groove 47, the articulating element 40 can articulate, but will be prevented from over-articulating or over-rotating such that the aperture 42 will remain visible through the side recess 22 during a surgical procedure. In other words, the motion limiting member 70 helps to prevent the articulating element 40 from over-articulating to such a degree that the aperture 42 faces the inside of the support body 14 whereby it would be unable to receive a mateable portion of a delivery instrument 100. Advantageously, while the motion limiting member 70 is in contact with the groove 47, the articulating element 40 can articulate through any angle up until the motion limiting member 70 contacts the end surface 49 of the groove (shown in FIG. 1). As shown in FIG. 1, the motion limiting member 70 can be a small cylindrical stump or peg that contacts the groove 47 of the articulating element, although it is not limited to this particular shape or size. For example, the motion limiting member 70 can be square or rectangular in shape.

To prevent the articulating element 40 from inadvertent back-out or removal from the support body 14, a blocking member 60 can be placed through aperture 64 to block and secure the articulating element 40 within the support body 14. The blocking member 60 can be inserted through an aperture 64 formed in the recess 22 of the support body 14. As shown in the illustrated embodiment, the blocking member 60 can comprise a cylindrical peg, although it is not limited to this shape or size. For example, in some embodiments, rather than be cylindrical in shape, the blocking member 60 can be rectangular in shape.

Figure 2A:
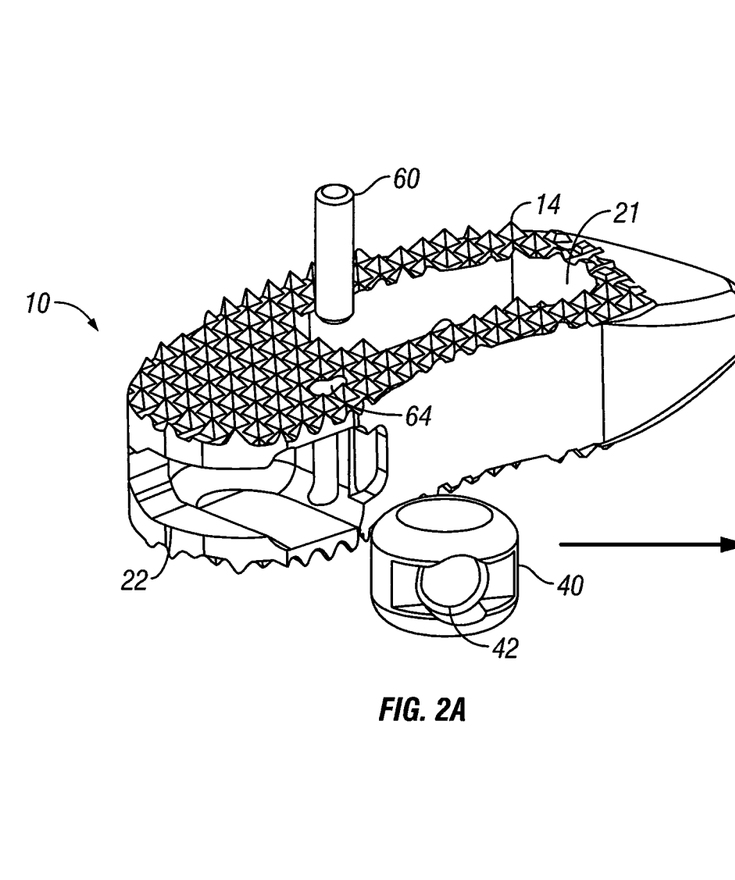
FIG. 2A is a perspective exploded view of an alternative implant having an articulating element with a bumper element according to some embodiments.

FIG. 2A is a perspective exploded view of an alternative implant having an articulating element with a bumper element according to some embodiments. Like the prior illustrated embodiment, the implant 10 includes a support body 14 having a side recess 22 for receiving an articulating element 40, an articulating element 40 including an aperture 42, and a blocking member 60 to prevent inadvertent back-out of the articulating element from the support body. However, in the present embodiment, the articulating element 40 includes a bumper element 84 (shown in FIGS. 2B and 2C) that prevents over-articulation or over-rotation of the articulating element 40 instead of a separate motion limiting member 70. Before the articulating element 40 is over-articulated or over-rotated, the bumper element 84 can contact an inner wall 25 within the support body 14 to prevent over-articulation. In some embodiments, the bumper element 84 sits in a groove or track 88 (shown in FIG. 2D) that allows for limited articulation, thereby advantageously preventing over-articulation.

Figure 2B:
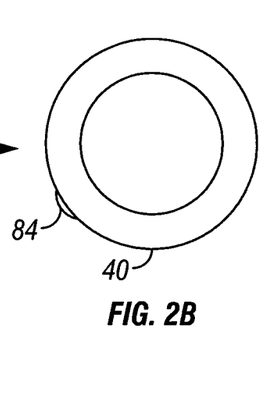
FIG. 2B is a top view of the articulating element of the implant in FIG. 2A.
Figure 2C:
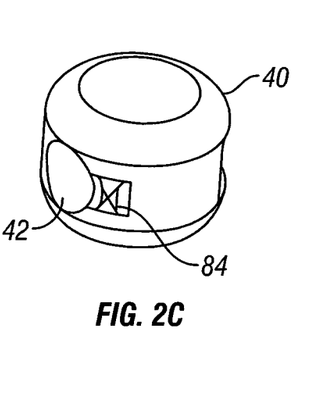
FIG. 2C is a side perspective view of the articulating element of the implant in FIG. 2A.
Figure 2D:
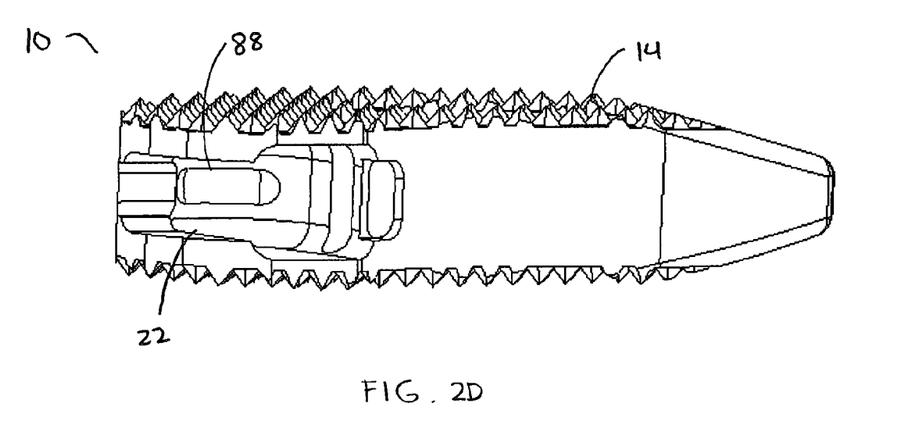
FIG. 2D is a cross-sectional view of the implant in FIG. 2A.

FIGS. 2B and 2C illustrate a bumper element 84 positioned on a surface of the articulating element 40. In some embodiments, the bumper element 84 comprises a protruding feature that extends from the surface of the articulating element 40. As shown in FIG. 2C, the bumper element 84 can be positioned near or adjacent the aperture 42. In other embodiments, the bumper element 84 can be positioned in other locations, such as away from the aperture 42 in other locations along the circumference of the articulating element. While the articulating element 40 in the illustrated embodiment includes a single bumper element 84, in other embodiments, the articulating element 40 includes two or more bumper elements 84. For example, an articulating element 40 can include two separate bumper elements 84, one on each side of the aperture 42, thereby preventing over-articulation or over-rotation in one or more directions. Furthermore, in some embodiments, the articulating element 40 can include a bumper element 84, yet still work in conjunction with a motion limiting member 70 as shown in FIG. 1.

Figure 3A:
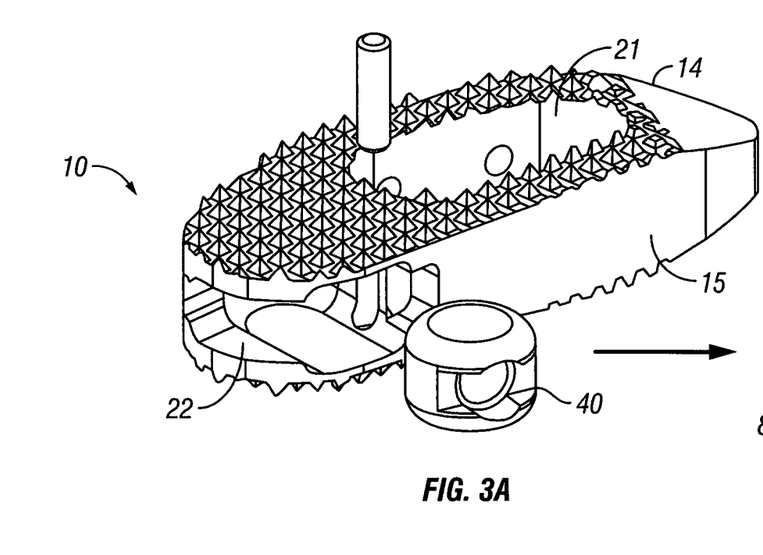
FIG. 3A is a perspective exploded view of an alternative implant having a support body with a substantially flat side surface according to some embodiments.
Figure 3B:
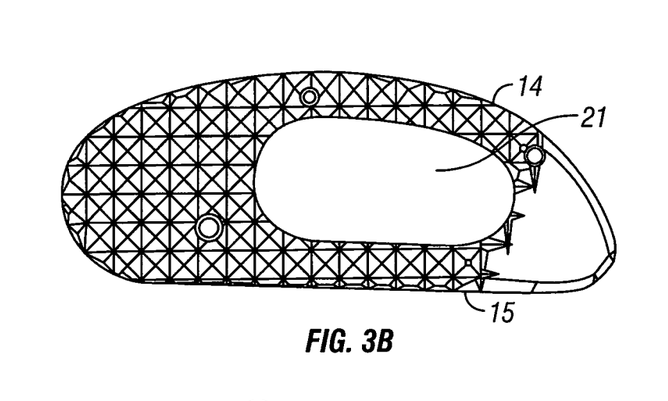
FIG. 3B is a top view of the implant in FIG. 3A.

FIG. 3A is a perspective exploded view of an alternative implant having a support body with a substantially flat side surface according to some embodiments. While the illustrated embodiment in FIG. 1 includes an implant 10 having a support body 14 with a recess 22 formed in a curved sidewall, the implant 10 in FIG. 3A includes a recess 22 formed in a sidewall that is substantially flat along at least a portion of the sidewall. The substantially flat portion of the sidewall 15 is visible in the top view in FIG. 3B. With the substantially flat portion of the sidewall 15, the support body 14 in FIG. 3A assumes less of a sickle-shape relative to the embodiment in FIG. 1. Advantageously, a surgeon can choose to use an implant 10 with a support body having a curved sidewall and sickle-shaped body as in FIG. 1, or an implant 10 with a support body having a substantially flat sidewall as in FIG. 3A, thereby providing greater options for the surgeon to address different body shapes. The different shape of the support body in FIG. 3A provides a different axial footprint that can cover a greater surface area compared to the support body in FIG. 1. In addition, the different shape also provides a larger graft opening.

Figure 3C:
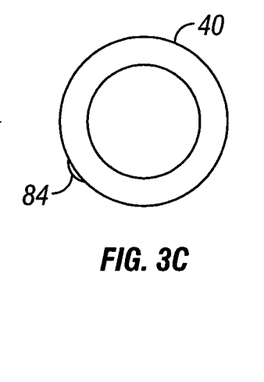
FIG. 3C is a top view of an articulating element of the implant in FIG. 3A.
Figure 3D:
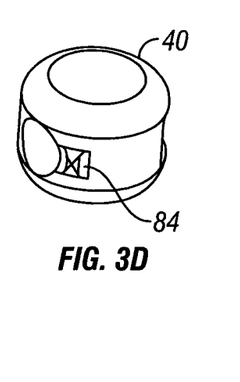
FIG. 3D is a side perspective view of the articulating element of the implant in FIG. 3A.

As shown in FIGS. 3C and 3D, the implant 10 can include an articulating element 40 having a bumper element 84 as discussed above. The bumper element 84 can advantageously help to prevent over-articulation or over-rotation of the articulating element 40 within the support body 14 having the substantially flat sidewall.

Figure 4:
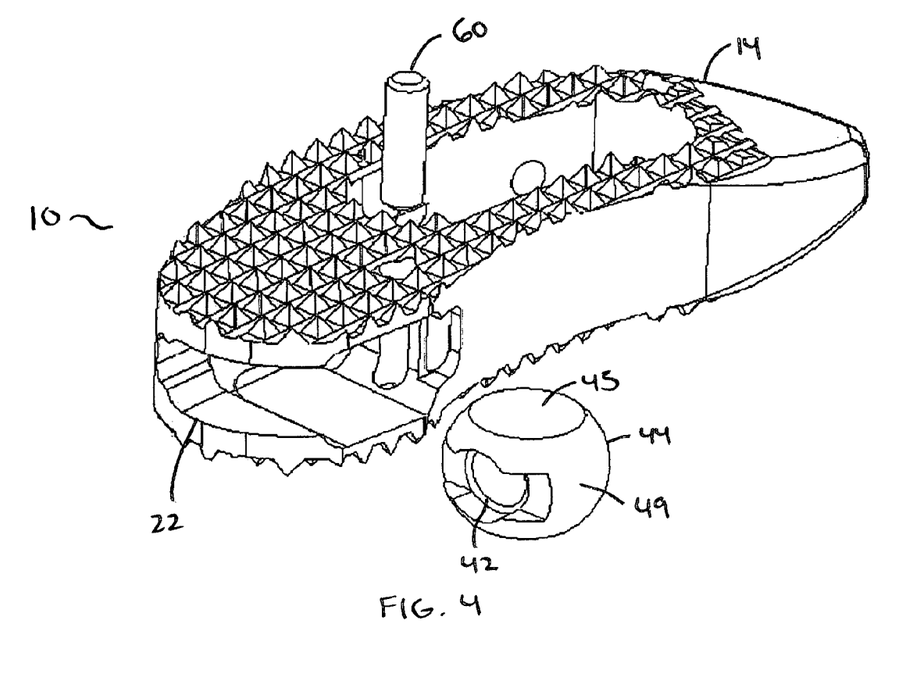
FIG. 4 is a perspective exploded view of an alternative implant having an articulating element with a substantially spherical body according to some embodiments.

FIG. 4 is a perspective exploded view of an alternative implant having an articulating element 44 with a substantially spherical body 49 according to some embodiments. The articulating element 44 in FIG. 4 has a more spherical shape with a rounder surface relative to the articulating element 40 in FIG. 1. Advantageously, the substantially spherical body of the articulating element 44 in FIG. 4 provides for increased articulation along one or more axes of rotation, thereby providing more flexibility in the placement of the support body 14 within a disc space. For example, in some embodiments, the articulating element 44 can move along a generally horizontal axis, as well as along other axes that intersect the horizontal axis. Like the articulating element 40 in FIG. 1, the articulating element 44 in FIG. 4 can be positioned in a recessed portion 22 formed within the support body 14.

Figure 5A:
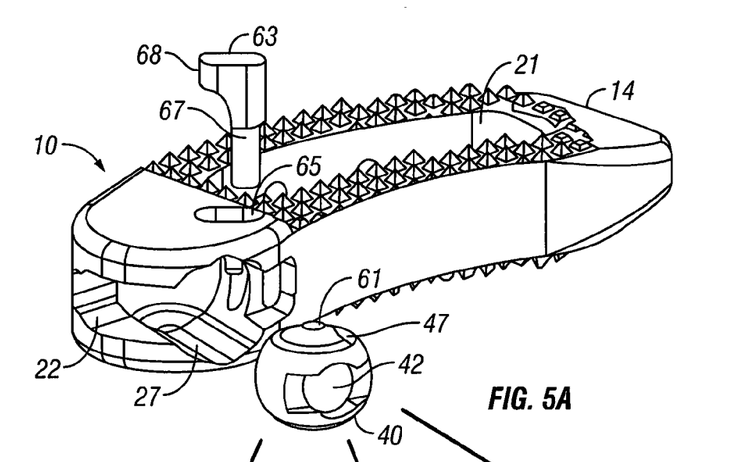
FIG. 5A is a perspective exploded view of an alternative implant having a combined blocking element and motion limiting element according to some embodiments.

FIG. 5A is a perspective exploded view of an alternative implant 10 having a combined blocking and motion limiting element 63 according to some embodiments. Like the illustrated implant in FIG. 1, the alternative implant 10 of FIG. 5A includes a support body 14 including a side recess 22 and an articulating element 40. In contrast, however, the alternative implant 10 includes a combined blocking and motion limiting element 63 that functions to prevent both the inadvertent back-out of the articulating element 40 and over-articulation of the articulating element 40.

As shown in FIG. 5A, the combined blocking and motion limiting element 63 includes a blocking post 67 that transitions into a motion limiting feature 68. The blocking post 67 helps to prevent the inadvertent back-out of the articulating member 40 from within the support body 14. The motion limiting feature 68, which is configured as an extension from the blocking post 67, can rest on the groove 47 to prevent over-articulation and/or over-rotation of the articulating element 40. The combined blocking and motion limiting element 63 can be delivered through an aperture 65 formed through a superior and/or inferior surface of the support body 14, as shown in FIG. 5A. The aperture 65 can be of a different size and shape compared to apertures 64 and 68 (in FIG. 1) to accommodate the features of the combined blocking and motion limiting element 63.

In addition, the articulating element 44 in FIG. 5A includes distinct features from the previously described articulating elements. In particular, in addition to having a substantially spherical body that advantageously provides for multi-axis articulation, the alternative articulating element 44 also includes a top bump-out feature 61 and a bottom bump-out feature 62 (shown in FIG. 5D). When the articulating element 44 is received in the recessed portion 22 of the support body 14, the top bump-out feature 61 and the bottom bump-out feature 62 can be received in one or more channels or grooves 27 formed within the support body 14. The grooves 27 advantageously allow for some rotation of the articulating element 44 along the longitudinal axis of the grooves, thereby providing articulation in multiple directions. In addition, the grooves help to limit the amount of rotation along the longitudinal axis of the grooves, thereby helping to prevent over-articulation in that rotational direction.

Figures 5B, 5C:
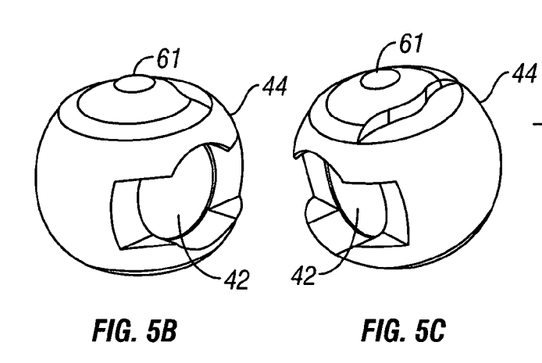
FIG. 5B is a side perspective view of an articulating element of the implant in FIG. 5A.
FIG. 5C is a different side perspective view of the articulating element of the implant in FIG. 5A.
Figure 5D:
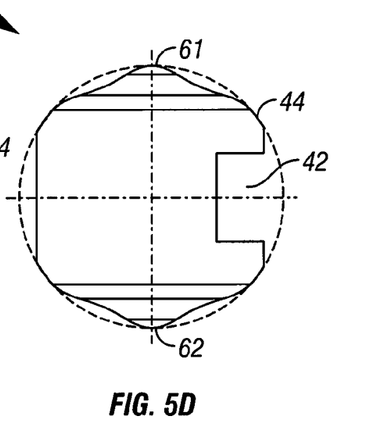
FIG. 5D is a cross-sectional view of the articulating element of the implant in FIG. 5A.

FIGS. 5B-5D more clearly illustrate the specific features of the articulating element 44, including the top bump-out feature 61 and the bottom bump-out feature 62. Of particular note is the cross-sectional view in FIG. 5D, in which it is shown that the shape of the articulating element 44 (including the top bump-out feature 61 and the bottom bump-out feature 62) generally conforms to a sphere, thereby allowing for maximum possible articulation and rotation within the support body 14.

Figure 6:
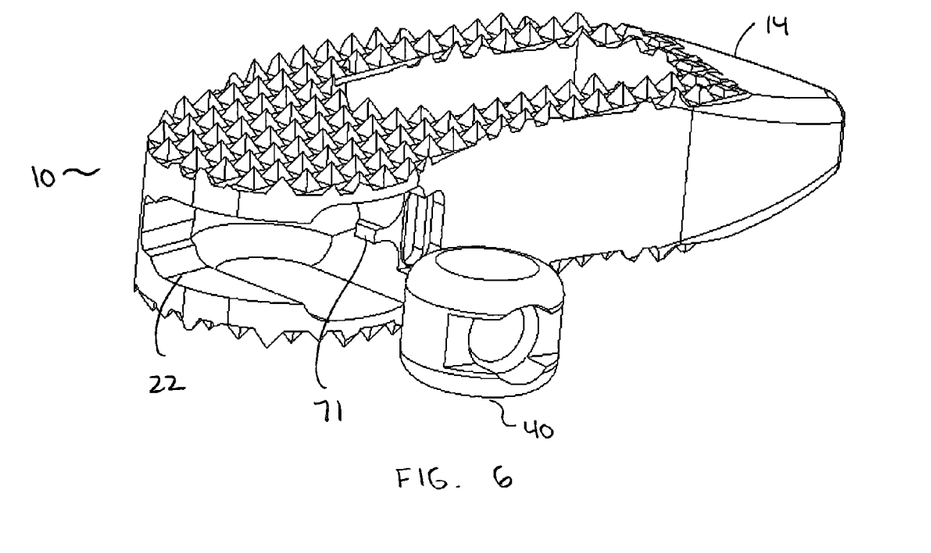
FIG. 6 is a perspective exploded view of an alternative implant having a support body with a built-in bumper element according to some embodiments.

FIG. 6 is a perspective exploded view of an alternative implant 10 having a support body 14 with a built-in bumper element 71 according to some embodiments. The built-in bumper element 71 can comprise a protruding surface that extends from an inner wall of the support body 14. In some embodiments, the built-in bumper element 71 helps to prevent inadvertent back-out of the articulating element 40 in the support body 14. As the bumper element 71 is built-in to the body of the support body 14, apertures for receiving a blocking member need not be formed through an end surface of the support body 14, thereby advantageously increasing the number of teeth 24 and/or surface area of teeth for contacting a vertebral surface.

Figure 7:
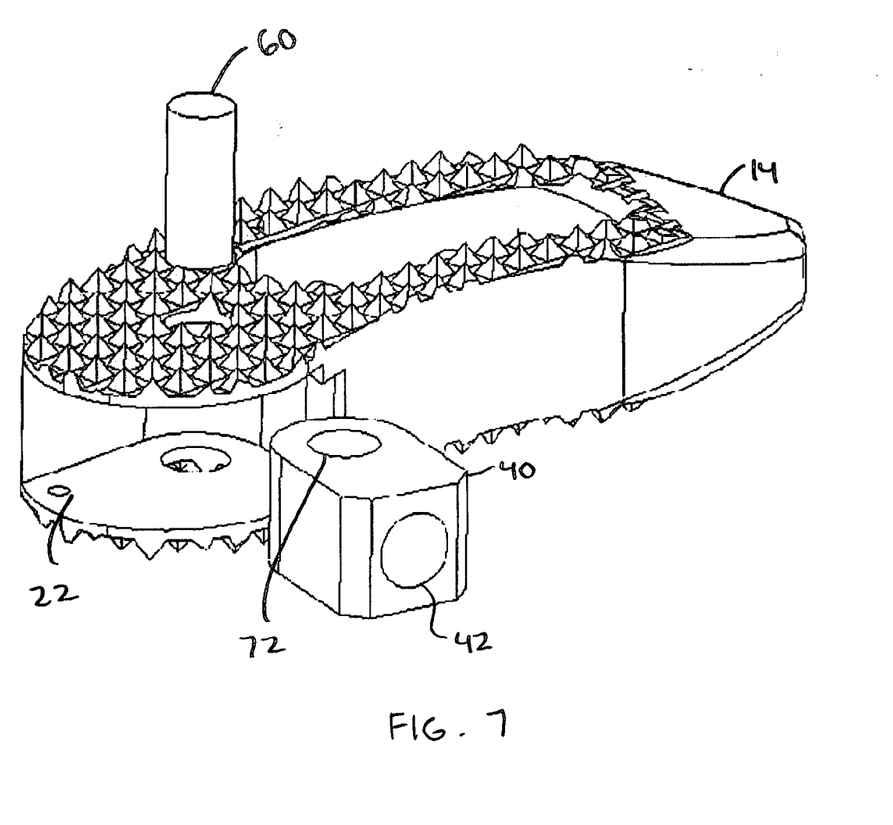
FIG. 7 is a perspective exploded view of an alternative implant having an articulating element configured to receive a retaining pin according to some embodiments.

FIG. 7 is a perspective exploded view of an alternative implant having an articulating element configured to receive a retaining pin according to some embodiments. The articulating element 40 includes an aperture 42 for receiving a portion of a delivery instrument, as well as an aperture or hole 72 formed therein for receiving a blocking member 60. When the articulating element 40 is positioned in the support body 14 and the blocking member 60 is inserted therein, the blocking member 60 serves as an axis of rotation about which the articulating element rotates.

Each of the novel implants described above provides an articulating element that can be articulated in one or more axes. In some embodiments, the articulating elements can be articulated between about 0 and 130 degrees, or between about 0 and 75 degrees along one or more axes.

Once a spacer implant is moved into a desired position between vertebrae, it is desirable for the implant to have sufficient structural rigidity or integrity such that the implant does not buckle or otherwise fail under loading by the spine. The implant should be configured so that it can sustain both axial compression and shear forces, as well as torsional forces. In some embodiments, the rigidity of the implant exceeds the rigidity of neighboring vertebral bodies to ensure that the implant does not collapse or fail under loading conditions.

The height of the spacer implant can vary depending upon the height of the area of the spine that is to be treated. In some embodiments, a variety of implants having different heights can be provided, thereby giving a surgeon multiple options of which implant to use. In other embodiments, the height of the implant can be adjusted within the disc space.

Any biocompatible material can be used to form all or part of a spacer implant of the present application. Suitable materials can include, but are not limited to, titanium, stainless steel and/or other surgical grade metals and metal alloys. In addition, various polymers, such as polyetheretherketone (PEEK), can also be used to form at least part of the spacer implant.

Methods of Use

The application encompasses a spacer implant having an articulating element that is loaded through a side cut-out section or recess of the spacer implant. The spacer implant can be implanted into a disc space between two vertebrae.

Various instruments can be provided to deliver the spacer implant in between two vertebrae. For example, in some embodiments, a delivery instrument or insertion tool as described in U.S. patent application Ser. No. 12/250,168 to Hansell et al., filed on Oct. 13, 2008 and hereby incorporated by reference in its entirety, can be used to deliver the spacer implant. The delivery instrument is capable of rigidly attaching to implant 10 and preventing rotation or articulation of the implant 10 with respect to the delivery instrument axis. When a surgeon desires to allow the implant to articulate with respect to the delivery instrument axis, a portion of the implant 10 can disengage from the delivery instrument to selectively allow the implant to articulate via an articulation element with respect to the delivery instrument axis. The implant can articulate to a desired position within a disc space, wherein it can be completely disengaged from the delivery instrument.

Figure 8A:
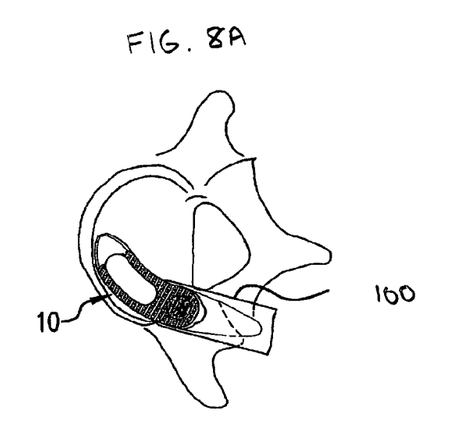
FIGS. 8A-8D illustrate a method of inserting an implant in a disc space using a delivery instrument according to some embodiments.
Figure 8B:
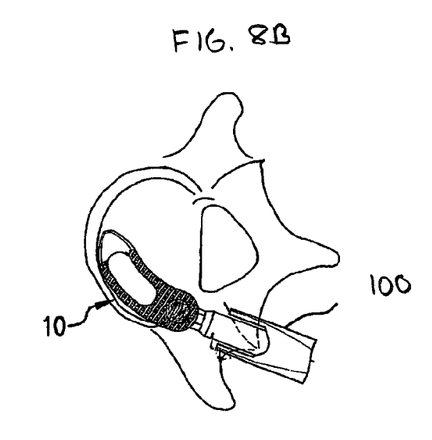
Figure 8C:
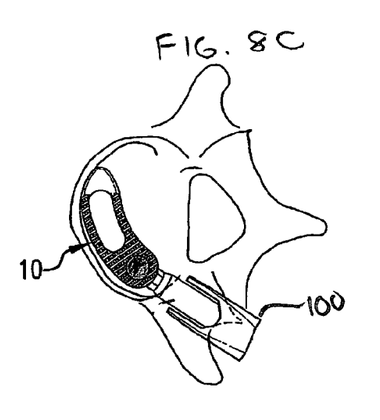
Figure 8D:
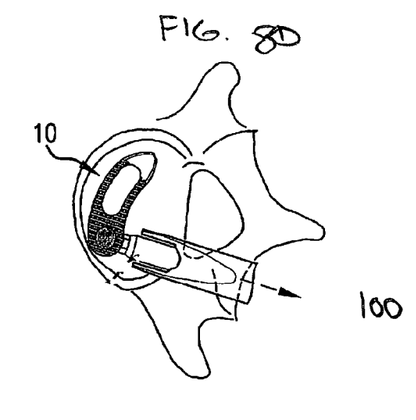

With reference to FIGS. 8A-8D, in some embodiments, the application encompasses methods for implantation comprising:

a. forming an incision in a patient;

b. attaching a spacer implant to a delivery instrument, wherein the spacer implant includes a superior end surface with teeth, an inferior end surface with teeth, a side recess therebetween and an articulating element positioned within the side recess, wherein the spacer implant is rigidly attached and incapable of articulating with respect to the delivery instrument axis;

c. delivering the delivery instrument and spacer implant through the incision to a disc space (FIG. 8A);

d. disengaging a portion of the spacer implant from the delivery instrument, thereby allowing the spacer implant with side recess to articulate via the articulating element with respect to the delivery instrument axis (FIG. 8B);

e. rotating the spacer implant via the articulating element relative to the delivery instrument until the spacer implant is in a desired position and orientation in a disc space (FIGS. 8C and 8D);

f. maintaining attachment of the spacer implant to at least a portion of the delivery instrument until the spacer implant is in the desired position; and g. disengaging the spacer implant completely from the delivery instrument and leaving the spacer implant within the body of the patient.

Any of the spacer implants 10 having side recesses for receiving an articulating element as described with respect to FIGS. 1-7 can be used with the methods described herein.

It will be apparent to those skilled in the art that various modifications and variations can be made in the present invention without departing from the scope or spirit of the invention. Moreover, the improved spacer implants and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed spacer implants. Thus, it is intended that the present invention cover the modifications and variations of this invention provided that they come within the scope of the appended claims or their equivalents.

What is claimed is:

1. A spinal implant comprising: a support body having a proximal end, a distal end, side surfaces connecting the proximal end with the distal end, a superior end surface and an inferior end surface, wherein each of the superior end surface and the inferior end surface include one or more teeth for contacting a superior and an inferior vertebrae; a side recess formed in the proximal end in between the superior end surface and the inferior end surface for receiving an articulating element therethrough; and an articulating element positioned in the recess, wherein the articulating element is configured to rotate along one or more axes after the articulating element is positioned in the recess; wherein the articulating element includes a substantially spherical body in contact with the recess, a top bump-out, and a connecting aperture adapted to be removably connected to a delivery tool.

2. The spinal implant of claim 1, wherein the support body includes a longitudinal opening for receiving bone graft.

3. The spinal implant of claim 1, further comprising a blocking member positioned in the recess to prevent inadvertent back-out of the articulating element.

4. The spinal implant of claim 3, wherein the blocking member comprises a cylindrical peg.

5. The spinal implant of claim 3, wherein the support body includes an aperture formed through either of the superior end surface or the inferior end surface for receiving the blocking member.

6. The spinal implant of claim 1, further comprising a motion limiting member for preventing over-articulation of the articulating element within the recess.

7. The spinal implant of claim 6, wherein the articulating element includes a groove that extends along a top portion of the articulating element, wherein the motion limiting member is configured to contact the groove.

8. The spinal implant of claim 6, wherein the support body includes an aperture formed through either of the superior end surface or the inferior end surface for receiving the motion limiting member.

9. The spinal implant of claim 1, wherein the support body includes a tapered distal end portion.

10. The spinal implant of claim 1, wherein the articulating element includes a bumper element.

11. The spinal implant of claim 1, further comprising a combined blocking and motion limiting element that is inserted into the support body.

12. The spinal implant of claim 1, wherein the support body includes a built-in bumper element.

13. A spinal implant comprising: a support body having a proximal end, a distal end, side surfaces connecting the proximal end with the distal end, a superior end surface and an inferior end surface for contacting a superior and an inferior vertebrae; a side recess formed in the proximal end in between the superior end surface and the inferior end surface for receiving an articulating element therethrough; an articulating element sized for insertion through the recess and configured to rotate along one or more axes after the articulating element is positioned in the recess; and a blocking member configured to be positioned within the recess for preventing back-out of the articulating element wherein the articulating element has a substantially spherical body in contact with the recess, with a top and bottom bump out and a connecting aperture adapted to be removably connected to a delivery tool.

14. The spinal implant of claim 13, wherein the superior end surface and the inferior end surface each include one or more teeth.

15. The spinal implant of claim 13, wherein the support body has a tapered distal portion.

16. The spinal implant of claim 13, wherein a top portion of the articulating element includes a groove for receiving a motion limiting element.

17. The spinal implant of claim 13, further comprising a motion limiting element configured to be placed in the support body to prevent over-articulation of the articulating element.

18. A spinal implant comprising:
a support body having a superior end surface and an inferior end surface, wherein each of the superior end surface and the inferior end surface includes one or more teeth, and wherein the support body includes a proximal end portion and a distal end portion having a tapered surface;
a longitudinal opening formed through the support body, wherein the longitudinal opening is configured to receive a bone graft material;
a side recess formed in the support body between the superior end surface and the inferior end surface;
an articulating element sized and shaped to be received in the recess, the articulating element including an aperture with threads for receiving a portion of an insertion tool and a groove on a top portion thereof;
a blocking member insertable through an aperture in the support body, the blocking member configured to prevent unintentional back-out of the articulating element from within the recess of the support body; and
a motion limiting member insertable through an aperture in the support body, the motion limiting member configured to contact the groove of the articulating element and to prevent over-articulation of the articulating element within the recess of the support body
wherein the articulating element is spherical and is configured with a top and bottom surface with bump outs.

* * * * *